United States Patent
Zhu

(10) Patent No.: US 6,577,983 B1
(45) Date of Patent: Jun. 10, 2003

(54) PRODUCE RECOGNITION METHOD

(75) Inventor: Jie Zhu, Fairport, NY (US)

(73) Assignee: NCR Corporation, Dayton, OH (US)

(*) Notice: Subject to any disclaimer, the term of this patent is extended or adjusted under 35 U.S.C. 154(b) by 68 days.

(21) Appl. No.: 09/684,414

(22) Filed: Oct. 6, 2000

(51) Int. Cl.$^7$ .............................................. G01D 1/00
(52) U.S. Cl. ................................................... 702/128
(58) Field of Search .................. 702/128; 235/463; 342/162; 395/135; 381/42; 233/462; 177/25, 50; 356/419, 416, 420, 226, 328; 250/226; 382/190, 110

(56) References Cited

U.S. PATENT DOCUMENTS

| | | | |
|---|---|---|---|
| 4,693,330 A | | 9/1987 | Uchimura et al. |
| 4,989,248 A | * | 1/1991 | Schalk et al. .................. 381/42 |
| 5,166,755 A | | 11/1992 | Gat |
| 5,375,195 A | * | 12/1994 | Johnston ...................... 395/135 |
| 5,401,949 A | * | 3/1995 | Ziemacki et al. ........... 235/463 |
| 5,546,475 A | | 8/1996 | Bolle et al. |
| 5,657,251 A | * | 8/1997 | Fiala .......................... 342/162 |
| 5,867,265 A | | 2/1999 | Thomas |
| 6,457,642 B1 | * | 10/2002 | Good et al. ............. 235/462.01 |

* cited by examiner

*Primary Examiner*—John Barlow
*Assistant Examiner*—Tung Lau
(74) *Attorney, Agent, or Firm*—Paul W. Martin; Priest & Goldstein, PLLC

(57) ABSTRACT

A produce recognition method which determines an optimal number of candidate identifications in a candidate identification list. The method includes the steps of obtaining produce data associated with a produce item, determining distances between the produce data and reference produce data, determining confidence values from the distances, determining first confidence values which are greater than a threshold confidence value, displaying candidate identifications associated with the first confidence values, and recording an operator choice of one of the candidate identifications.

7 Claims, 3 Drawing Sheets

PRODUCE RECOGNITION METHOD

CROSS-REFERENCE TO RELATED APPLICATIONS

The present invention is related to the following commonly assigned and co-pending U.S. applications:

"A Produce data collector And A Produce Recognition System", filed Nov. 10, 1998, invented by Gu, and having a Ser. No. 09/189,783; and "Produce Recognition System and Method", filed Jul. 28, 1999, invented by Gu, and having a Ser. No. 09/362,488.

BACKGROUND OF THE INVENTION

The present invention relates to product checkout devices and more specifically to a produce recognition method.

Bar code readers are well known for their usefulness in retail checkout and inventory control. Bar code readers are capable of identifying and recording most items during a typical transaction since most items are labeled with bar codes.

Items which are typically not identified and recorded by a bar code reader are produce items, since produce items are typically not labeled with bar codes. Bar code readers may include a scale for weighing produce items to assist in determining the price of such items. But identification of produce items is still a task for the checkout operator, who must identify a produce item and then manually enter an item identification code. Operator identification methods are slow and inefficient because they typically involve a visual comparison of a produce item with pictures of produce items, or a lookup of text in table. Operator identification methods are also prone to error, on the order of fifteen percent.

A produce recognition system is disclosed in the cited co-pending application. A produce item is placed over a window in a spectral data collector, the produce item is illuminated, and the spectrum of the diffuse reflected light from the produce item is measured. A terminal compares the spectrum to reference spectra in a library to determine a list of candidate identifications.

Finding an appropriate length for the list is important in order to achieve optimal speed without sacrificing accuracy. If the list is too long, the operator may take longer than necessary to find a matching candidate. If the list is too short, the matching candidate could be left out, leaving the operator unable to find it. The operator may also choose incorrectly.

Therefore, it would be desirable to provide a produce recognition method with improved selection speed and accuracy.

SUMMARY OF THE INVENTION

In accordance with the teachings of the present invention, a produce recognition method is provided.

The method includes the steps of obtaining produce data associated with a produce item, determining distances between the produce data and reference produce data, determining confidence values from the distances, determining first confidence values which are greater than a threshold confidence value, displaying candidate identifications associated with the first confidence values, and recording an operator choice of one of the candidate identifications.

It is accordingly an object of the present invention to provide a produce recognition method.

It is another object of the present invention to provide a method of improving selection speed and accuracy of produce choices in a produce recognition system.

It is another object of the present invention to determine an optimal number of candidate identifications in a candidate identification list.

BRIEF DESCRIPTION OF THE DRAWINGS

Additional benefits and advantages of the present invention will become apparent to those skilled in the art to which this invention relates from the subsequent description of the preferred embodiments and the appended claims, taken in conjunction with the accompanying drawings, in which:

DETAILED DESCRIPTION OF THE PREFERRED EMBODIMENT

Figure 1:
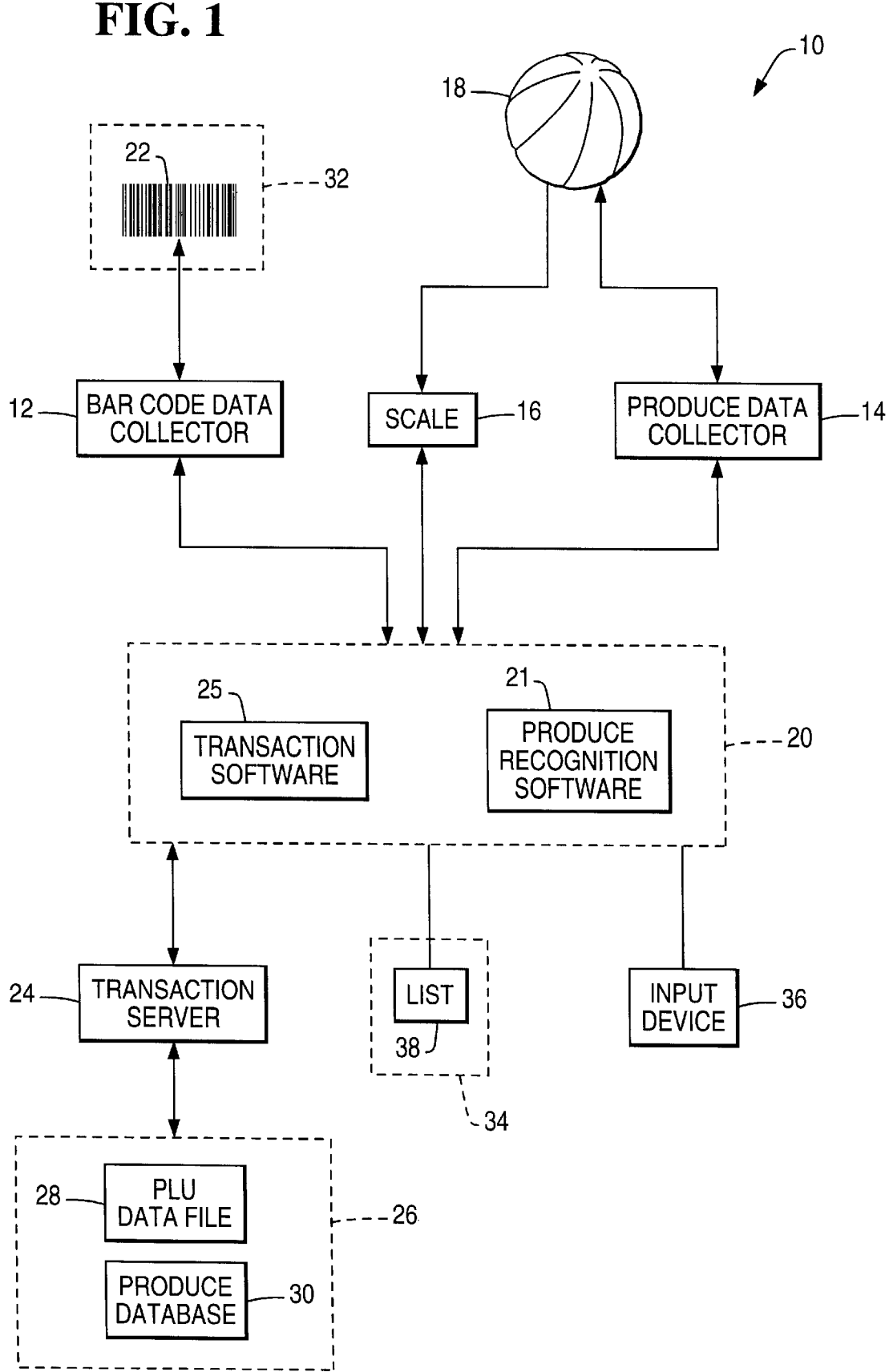
FIG. 1 is a block diagram of a transaction processing system including a produce recognition system.

Referring now to FIG. 1, transaction processing system 10 includes bar code data collector 12, produce data collector 14, and scale 16.

Bar code data collector 12 reads bar code 22 on merchandise item 32 to obtain an item identification number, also know as a price look-up (PLU) number, associated with item 32. Bar code data collector 12 may be any bar code data collector, including an optical bar code scanner which uses laser beams to read bar codes. Bar code data collector 12 may be located within a checkout counter or mounted on top of a checkout counter.

Produce data collector 14 collects data for produce item 18. Such data may include color and color distribution data, size data, shape data, surface texture data, and aromatic data. Reference produce data is collected and stored within produce database 30.

Transaction terminal 20 and produce data collector 14 are the primary components of the produce recognition system.

During a transaction, produce data collector 14 may be self-activated upon a drop of ambient light, or operation may be initiated by placement of produce item 18 on scale 16 or by operator commands.

Scale 16 determines a weight for produce item 18. Scale 16 works in connection with bar code data collector 12, but may be designed to operate and be mounted separately. Scale 16 sends weight information for produce item 18 to transaction terminal 20 so that transaction terminal 20 can determine a price for produce item 18 based upon the weight information.

Bar code data collector 12 and produce data collector 14 operate separately from each other, but may be integrated together. Bar code data collector 12 works in conjunction with transaction terminal 20 and transaction server 24. Scale 16 may also work in connection with bar code data collector 12, but may be designed to operate and be mounted separately.

Storage medium 26 preferably includes one or more hard disk drives. Produce database 30 is preferably stored within storage medium 26, but may also be located instead at transaction terminal 20. PLU data file 28 is stored within storage medium 26, but may be located instead at transaction terminal 20 or bar code data collector 12.

Display 34 and input device 36 may be part of a touch screen or located separately.

In the case of bar coded items, transaction terminal 20 obtains the item identification number from bar code data collector 12 and retrieves a corresponding price from PLU data file 28 through transaction server 24.

In the case of non-bar coded produce items, transaction terminal 20 executes produce recognition software 21 which obtains produce characteristics of produce item 18 from produce data collector 14, identifies produce item 18 by comparing produce data in produce database 30 with collected produce data, and retrieves an item identification number from produce database 30 and passes it to transaction software 25, which obtains a corresponding price from PLU data file 28.

In an alternative embodiment, preliminary identification of produce item 18 may be handled by transaction server 24. Transaction server 24 receives collected produce characteristics and compares them with produce data in produce database 30. Transaction server 24 provides a candidate list to transaction terminal 20 for display and final selection. Following identification, transaction server 24 obtains a price for produce item 18 and forwards it to transaction terminal 20.

To assist in proper identification of produce items, produce recognition software 21 additionally displays candidate identifications in list 38 for operator selection and verification. Produce recognition software 21 preferably arranges the candidate identifications in terms of probability of match and displays their images in predetermined locations on operator display 34 of transaction terminal 20. The operator may accept the most likely candidate returned by produce recognition software 21 or override it with a different choice using input device 36.

Figure 2:
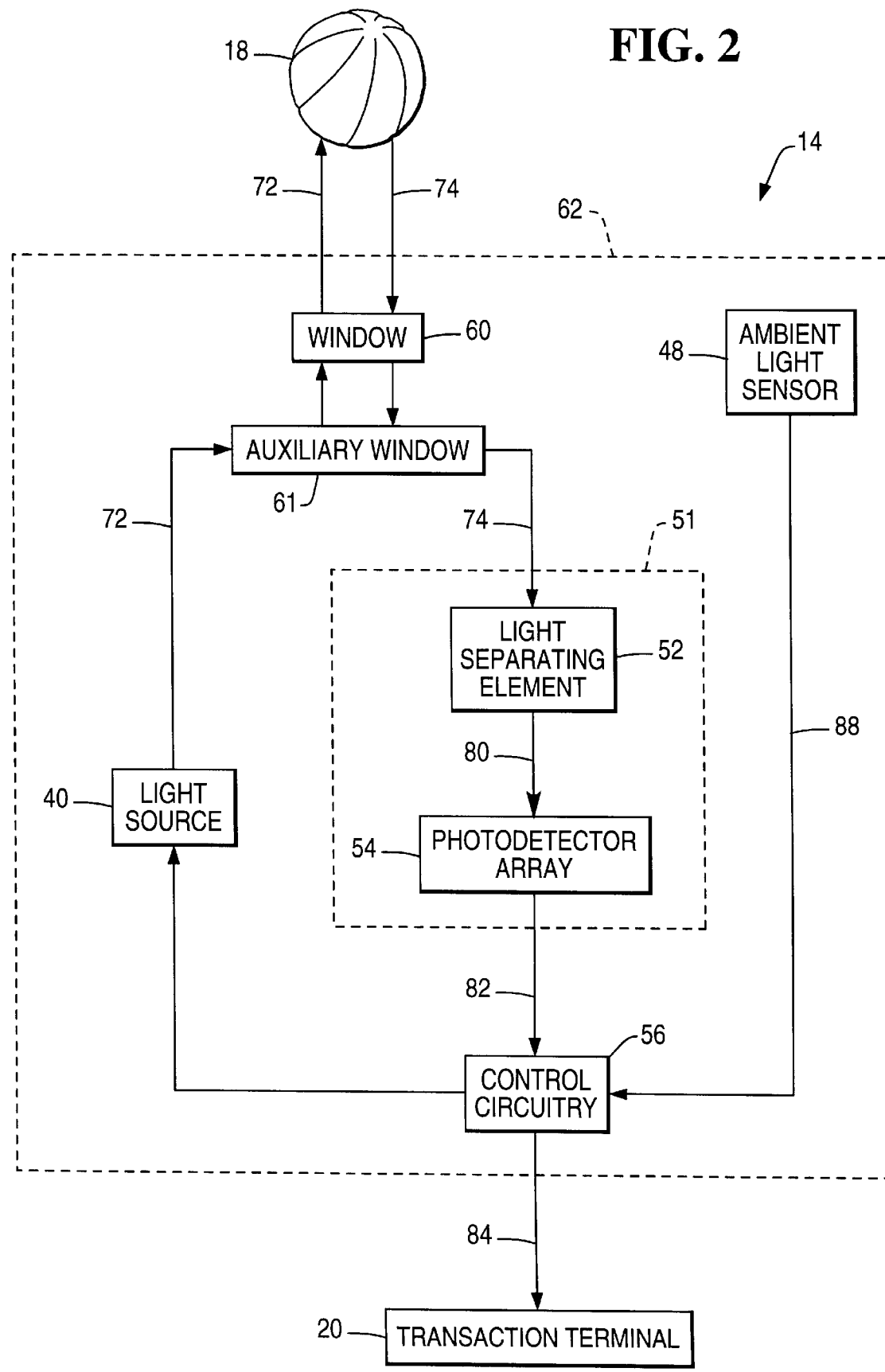
FIG. 2 is a block diagram of a type of produce data collector.

Turning now to FIG. 2, an example produce data collector 14 which relies on spectroscopic analysis is illustrated. Other types of produce data collectors are also envisioned.

Example produce data collector 14 primarily includes light source 40, spectrometer 51, control circuitry 56, transparent window 60, and housing 62.

Light source 40 produces light 70. Light source 40 preferably produces a white light spectral distribution, and preferably has a range from four hundred 400 nm to 700 nm, which corresponds to the visible wavelength region of light.

Light source 40 preferably includes one or more light emitting diodes (LEDs). A broad-spectrum white light producing LED, such as the one manufactured by Nichia Chemical Industries, Ltd., is preferably employed because of its long life, low power consumption, fast turn-on time, low operating temperature, good directivity. Alternate embodiments include additional LEDs having different colors in narrower wavelength ranges and which are preferably used in combination with the broad-spectrum white light LED to even out variations in the spectral distribution and supplement the spectrum of the broad-spectrum white light LED.

Other types of light sources 40 are also envisioned by the present invention, although they may be less advantageous than the broad spectrum white LED. For example, a tungsten-halogen light may be used because of its broad spectrum, but produces more heat.

A plurality of different-colored LEDs having different non-overlapping wavelength ranges may be employed, but may provide less than desirable collector performance if gaps exist in the overall spectral distribution.

Ambient light sensor 48 senses the level of ambient light through windows 60 and 61 and sends ambient light level signals 81 to control circuitry 56. Ambient light sensor 48 is mounted anywhere within a direct view of window 61.

Spectrometer 51 includes light separating element 52 and photodetector array 54.

Light separating element 52 splits light 74 in the preferred embodiment into light 80 of a continuous band of wavelengths. Light separating element 52 is preferably a linear variable filter (LVF), such as the one manufactured by Optical Coating Laboratory, Inc., or may be any other functionally equivalent component, such as a prism or a grating.

Photodetector array 54 produces waveform signals 82 containing spectral data. The pixels of the array spatially sample the continuous band of wavelengths produced by light separating element 52, and produce a set of discrete signal levels. Photodetector array 54 is preferably a complimentary metal oxide semiconductor (CMOS) array, but could be a Charge Coupled Device (CCD) array.

Control circuitry 56 controls operation of produce data collector 14 and produces digitized produce data waveform signals 84. For this purpose, control circuitry 56 includes an analog-to-digital (A/D) converter. A twelve bit A/D converter with a sampling rate of 22–44 kHz produces acceptable results.

Transparent window 60 is mounted above auxiliary transparent window 61. Windows 60 and 61 include an anti-reflective surface coating to prevent light 72 reflected from windows 60 and 61 from contaminating reflected light 74.

Housing 62 contains light source 40, ambient light sensor 48, spectrometer 51, photodetector array 54, control circuitry 56, auxiliary transparent window 61, and transparent window 60.

Figure 3:
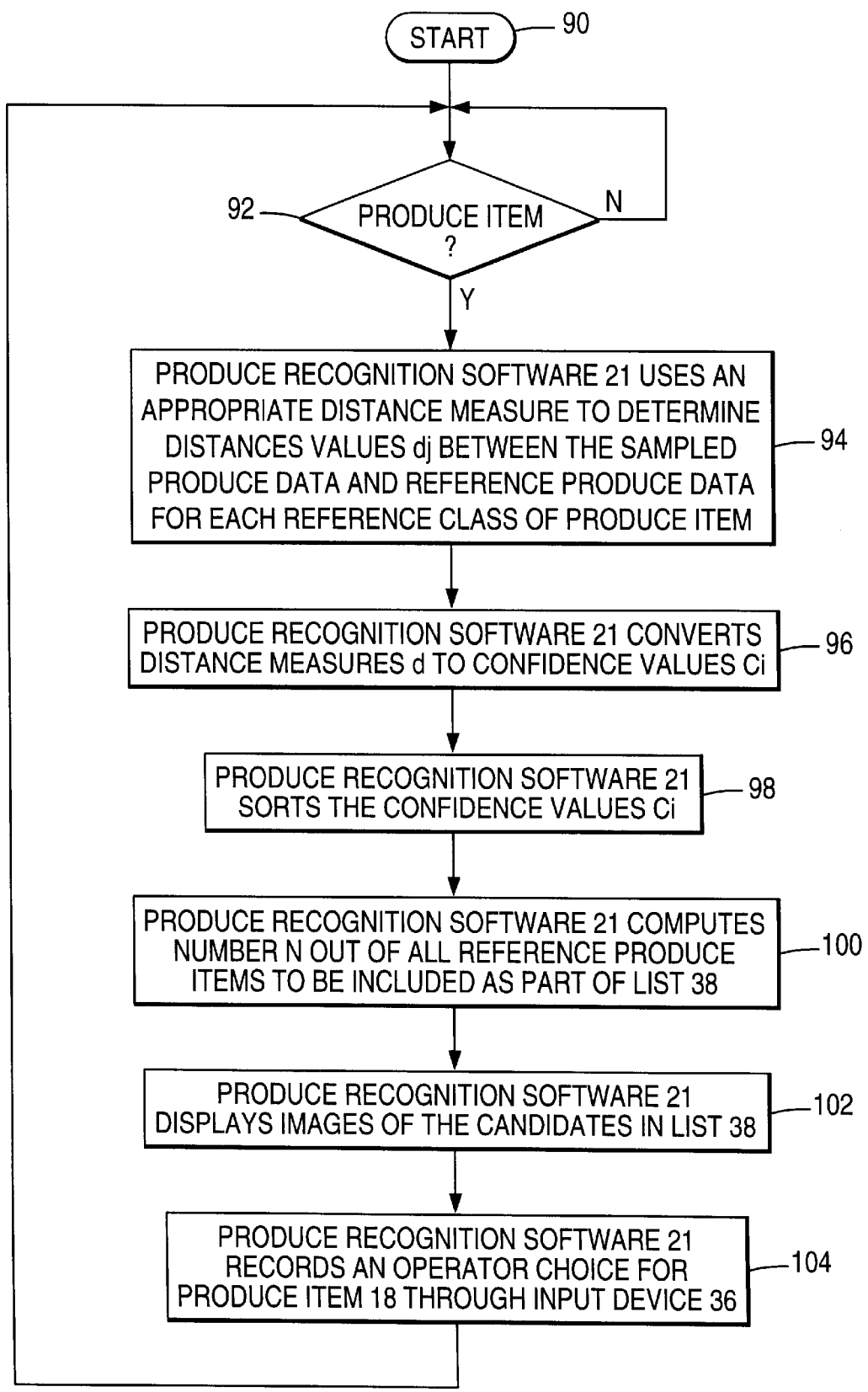
FIG. 3 is a flow diagram illustrating the produce recognition method of the present invention.

Turning now to FIG. 3, the produce recognition method of the present invention begins with START 90.

In step 92, produce recognition software 21 waits for produce data from produce data collector 14. Produce data may include spectral or other types of data and may include combinations of different types of data. Operation proceeds to step 94 following produce data collection.

In step 94, produce recognition software 21 uses an appropriate distance measure to determine distance values $d_j$ between the sampled produce data and reference produce data for each reference class of produce item.

For example, using a nearest neighbor algorithm, a distance is computed from the sampled produce data to each matching template of a class of produce item.

Another example distance measure is the distance measure of likeness (DML) defined in the second-listed co-pending application by Gu. A DML value provides a distance between an unknown instance and a class of produce item, with the smallest DML value yielding the most likely candidate:

$$DML \equiv d_{ij} = \sqrt{\frac{\sum_{k=1}^{n_j} (x_{ijk} - x_{tik})^2}{n_j}},$$

where $n_j$ is the number of instances in the j-th class, k is an integer from 1 to $n_j$, distance is measured in the i-th dimension, $X_{ijk}$ are the coordinates of a sampled instance, and $X_{tik}$ are the coordinates of a typical reference instance.

In step 96, produce recognition software 21 converts distance measures $d_j$ to confidence values $C_j$:

$$C_i = \frac{\frac{1}{d_i}}{\sum_{j=1}^{N} \frac{1}{d_j}},$$

where N is the total number of classes of reference produce items.

In step 98, produce recognition software 21 sorts the confidence values $C_i$.

In step 100, produce recognition software 21 computes number N out of all reference produce items to be included as part of list 38 so that:

$$\sum_{i=1}^{N} C_i \geq T,$$

where T is a threshold, so that there is a T probability that produce item 18 is within list 38. List 38 is a truncated list of all reference produce items.

In step 102, produce recognition software 21 displays images of the candidates in list 38.

In step 104, produce recognition software 21 records an operator choice for produce item 18 through input device 36.

Transaction terminal 20 uses the identification information to obtain a unit price for produce item 18 from transaction server 24. Transaction terminal 20 then determines a total price by multiplying the unit price by weight information from scale 16. Operation returns to step 92 to prepare for another produce item.

Although the invention has been described with particular reference to certain preferred embodiments thereof, variations and modifications of the present invention can be effected within the spirit and scope of the following claims.

I claim:

1. A produce recognition system for recognizing a non-bar coded produce item comprising:
   a storage medium having a produce database and a look up data file, the produce database stores reference produce data items and item identification numbers;
   a produce data collector for receiving light data reflected from the non-bar coded produce item and converting the light data to a digitized collected produce data;
   wherein the produce data collector includes
      a housing;
      a window mounted within the housing; and
      a light source having one or more light emitted diodes for producing a white light spectral distribution, the white light transmitted through the window on to the non-bar coded produce item to create a reflected light;
      spectrometer having a light-separating element and a photodetector array, the light separating element converts the reflected light received through the window to a continuous band of wavelengths, the photodetector array spatially samples the continuous band of wavelengths to produce discrete signal levels; and
      a control circuit converts the discrete signal levels to digitized produce data;
   a transaction software component;
   a processor and produce recognition software for comparing the digitized collected produce data with the reference produce data items, retrieving the item identification number for the non-bar coded produce item on a successful match of the digitized collected produce data and the reference produce data item, and obtaining a corresponding price for the non-bar coded item from the look up data file; and
   a display for displaying the price retrieved from the look up data file.

2. A produce recognition system for recognizing a non-bar coded produce item comprising:
   a storage medium having a produce database, the produce database stores reference produce data items;
   a produce data collector for receiving light data reflected from the non-bar coded produce item and converting the light data to a digitized collected produce data;
   wherein the produce data collector includes
      a housing;
      a window mounted within the housing;
      a light source having one or more light emitted diodes for producing a white light spectral distribution, the white light transmitted through the window on to the non-bar coded produce item to create a reflected light;
      a spectrometer having a light separating element and a photodetector array, the light separating element converts the reflected light received through the window to a continuous band of wavelengths, the photodetector array spatially samples the continuous band of wavelengths to produce discrete signal levels; and
      a control circuit converts the discrete signal levels to digitized produce data;
   a transaction software component;
   a processor and produce recognition software comparing the digitized collected produce data with reference produce data items to define a candidate list of reference data describing like produce, the candidate list having a confidence interval for each chosen reference produce data item and sorted thereby, each chosen reference produce data item is chosen by a distance measuring algorithm, the list size determined by summing the confidence values to a value greater than or equal to a threshold probability representing success; and
   a display for displaying the candidate list and allowing the operator to choose from the list.

3. A produce recognition system as in claim 1 wherein the produce data collector further comprises:
   an ambient light sensor mounted within the housing and in direct view of the window, the sensor receives ambient light through the window and sends signals to the control circuit to begin transmitting light data at the produce item.

4. A produce recognition system as in claim 2 wherein the produce data collector further comprises:
   an ambient light sensor mounted within the housing and in direct view of the window, the sensor receives ambient light through the window and sends signals to the control circuit to begin transmitting light data at the produce item.

5. A non-bar coded produce recognition method comprising the steps of:
   (a) receiving light spectral data describing the produce item;
   (b) converting the light spectral data to digitized collected produce data;
   (c) comparing the digitized collected produce data with the reference produce data stored in the produce database, on a successful match an item identification number associated with the reference produce data is passed to a transaction software component, the transaction software component obtaining a corresponding unit price from a look up data file;

(d) obtaining weight information associated with the produce item: and (e) calculating the overall produce data cost by multiplying the unit price by weight information.

6. A non-bar coded produce recognition method comprising the steps of:

(a) receiving light spectral data reflected off of the produce item;

(b) converting the light spectral data to a digitized collected produce data;

(c) comparing the digitized collected produce data with reference produce data items stored in a produce database to define a sorted candidate list of reference data items, the candidate list having a confidence interval for each chosen reference produce data item within the list, each chosen reference produce data chosen by a distance measuring algorithm, the list size determined by summing the confidence values to a value greater than or equal to a threshold probability representing success;

(d) displaying the list;

(e) recording an operator choice for a selected item from a input device;

(f) obtaining a unit price for the selected item;

(g) obtaining weight information associated with the produce from a scale; and (h) calculating the overall produce data cost by multiplying the unit price by the weight information.

7. A non-bar coded produce recognition method comprising the steps of:

(a) receiving light spectral data reflected off of the produce item;

(b) converting the light spectral data to a digitized collected produce data;

(c) comparing the digitized collected produce data with reference produce data items stored in a produce database to define a sorted candidate list of reference data items, the candidate list having a confidence interval for each chosen reference produce data item within the list, each chosen reference produce data chosen by a distance measuring algorithm, the list size determined by summing the confidence values to a value greater than or equal to a threshold probability representing success; and (d) displaying the list and images associated with each entry in the list.

* * * * *